(12) United States Patent
Forsell

(10) Patent No.: US 10,881,579 B2
(45) Date of Patent: *Jan. 5, 2021

(54) APPARATUS FOR THE TREATMENT OF FEMALE SEXUAL DYSFUNCTION

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/495,655

(22) Filed: Apr. 24, 2017

(65) Prior Publication Data

US 2017/0361109 A1    Dec. 21, 2017

Related U.S. Application Data

(63) Continuation of application No. 14/827,560, filed on Aug. 17, 2015, now Pat. No. 9,629,775, which is a continuation of application No. 14/094,402, filed on Dec. 2, 2013, now Pat. No. 9,107,796, which is a continuation of application No. 13/384,387, filed on Jan. 17, 2012, now Pat. No. 9,610,455, which is a continuation of application No. 13/122,907, filed as application No. PCT/SE2009/051128 on Oct. 9, 2009, now Pat. No. 8,600,510.

(60) Provisional application No. 61/227,812, filed on Jul. 23, 2009.

(30) Foreign Application Priority Data

Oct. 10, 2008 (SE) ........................... 0802151

(51) Int. Cl.
*A61N 1/36* (2006.01)
*A61H 19/00* (2006.01)
*A61N 1/378* (2006.01)
*A61N 1/05* (2006.01)
*A61N 1/372* (2006.01)
*H02J 5/00* (2016.01)

(52) U.S. Cl.
CPC .............. *A61H 19/34* (2013.01); *A61H 19/40* (2013.01); *A61N 1/36007* (2013.01); *A61N 1/3787* (2013.01); *A61H 2201/5097* (2013.01); *A61N 1/0524* (2013.01); *A61N 1/37252* (2013.01); *H02J 5/005* (2013.01)

(58) Field of Classification Search
CPC .............. A61N 1/36007; A61N 1/0551; A61N 1/0524; A61N 1/36107; A61N 1/37205; A61N 1/372; A61N 1/05; A61N 1/36021; A61N 1/0521; A61N 1/0558; A61N 1/3787; A61N 2005/0608; A61N 2005/0611; A61B 2018/00559
See application file for complete search history.

(56) References Cited

U.S. PATENT DOCUMENTS 8,795,153 B2 * 8/2014 Forsell .............. A61F 6/20 600/38
9,629,775 B2 * 4/2017 Forsell ............... A61N 1/36007
10,568,804 B2 * 2/2020 Forsell ............ 606/193
(Continued)

*Primary Examiner* — Rex R Holmes

(57) ABSTRACT

There is disclosed an apparatus for treating a sexual dysfunctional female patient, comprising an implanted stimulation device adapted to stimulate at least a part of the vagina of the patient by movement of said stimulation device and contact between said stimulation device and the sexually responsive tissue or the wall of the vagina. A system and an operation method for the treatment of female sexual dysfunction are also disclosed.

17 Claims, 12 Drawing Sheets

(56) References Cited

U.S. PATENT DOCUMENTS

| | | | |
|---|---|---|---|
| 2002/0120219 A1* | 8/2002 | Hovland | A61F 5/48 |
| | | | 601/6 |
| 2007/0123809 A1* | 5/2007 | Weiss | A61H 21/00 |
| | | | 601/84 |
| 2007/0191766 A1* | 8/2007 | McMorrow | A61M 25/10 |
| | | | 604/103.01 |
| 2009/0082705 A1* | 3/2009 | Asfora | A61H 19/00 |
| | | | 601/46 |

* cited by examiner

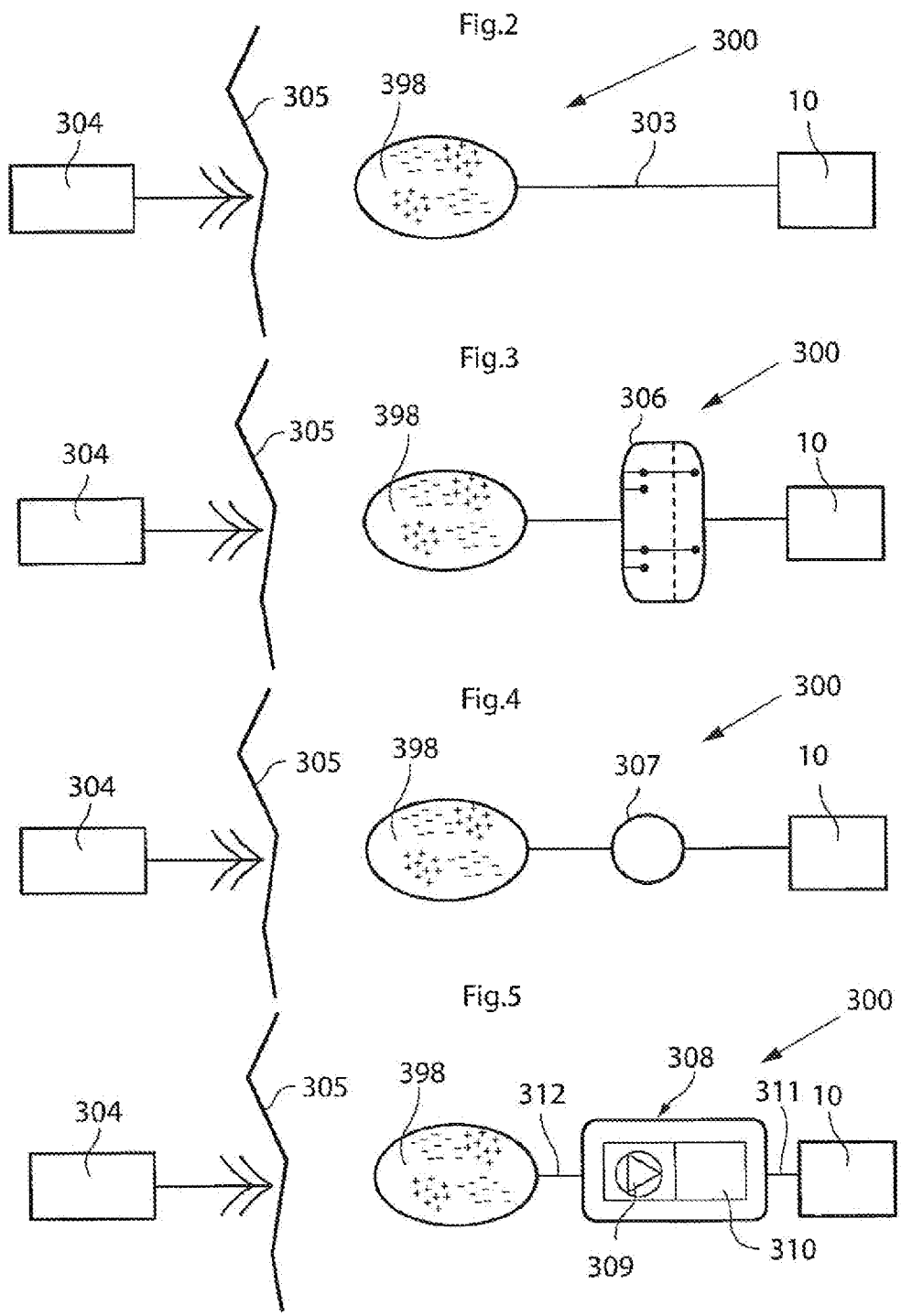

Fig.24
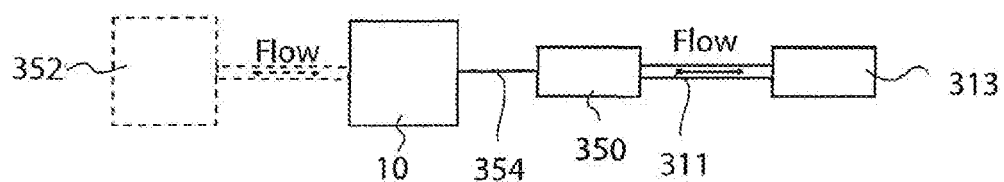
Fig.25 a
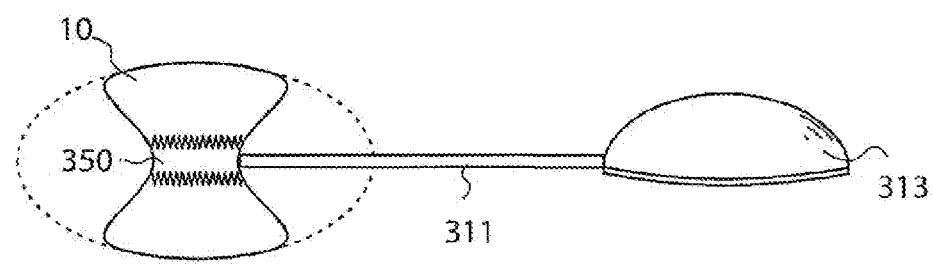
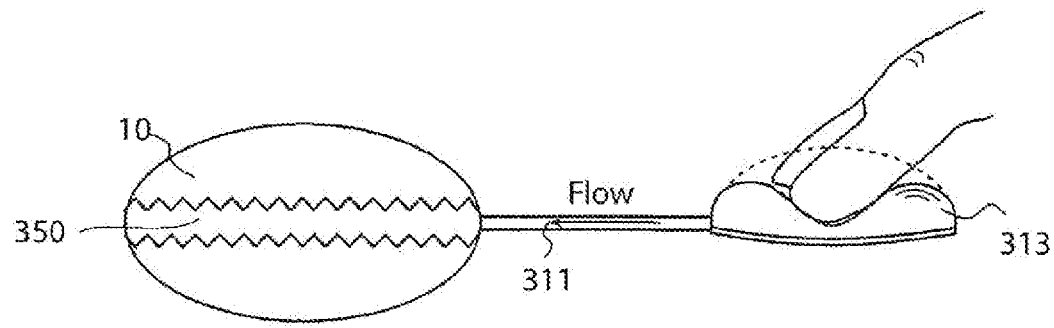
Fig.25 c
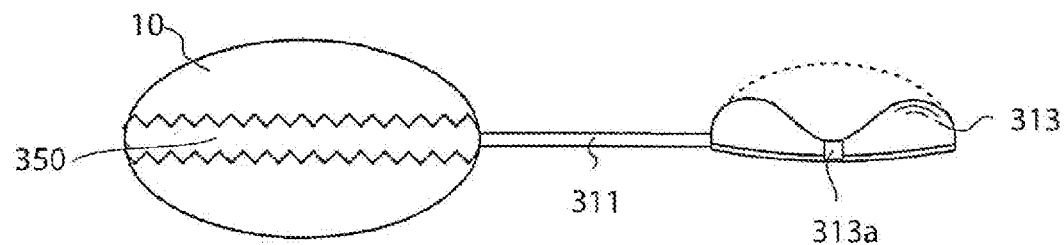

APPARATUS FOR THE TREATMENT OF FEMALE SEXUAL DYSFUNCTION

This application is a continuation of U.S. patent application Ser. No. 14/827,560, filed Aug. 17, 2015, and issued as U.S. Pat. No. 9,629,775 which is a continuation of U.S. patent application Ser. No. 14/094,402, filed Dec. 2, 2013, and issued as U.S. Pat. No. 9,107,796, which is a continuation of U.S. patent application Ser. No. 13/122,907, filed Apr. 6, 2011, and issued as U.S. Pat. No. 8,600,510, which is the U.S. National Phase of International Application No. PCT/SE2009/051128, filed 9 Oct. 2009, which designated the U.S. and claims the priority from Swedish Application No. 0802151-1, filed Oct. 10, 2008, and claims the benefit of U.S. Provisional Application No. 61/227,812, filed on 23 Jul. 2009, the entire contents of each of which are hereby incorporated by reference in this application.

TECHNICAL FIELD

The present invention relates to the treatment of female sexual dysfunction

BACKGROUND

A lot of attention has been given to male sexual disorders including impotency. This has lead to the availability of a number of treatment options for males, including pharmaceuticals such as Viagra.

In contrast, there is a lack of therapies for treating female sexual dysfunction. Female sexual dysfunction such as disorders of sexual desire, arousal or orgasm is a common problem, affecting up to 43% of all women (Pauls et al, Obstret Gynecol Surv, 2005 60(3):3196-205). Both biological and psychological factors contribute to FSD.

Available treatments include psychological counselling to pairs or individuals. Where side effects of medication contributes to FSD, altering medication or dosage may help. However, there is a need for improved treatment of FSD.

During sexual arousal of the female, vasocongestion of the pelvic region leads to engorgement of the genitalia with blood leading to swelling of the external genitalia and erection of the clitoris. This is accompanied by lubrication of the vagina. In the female, the corpus cavernosa are two paired symmetrical extensions of the clitoris and engorgement of these is an important step during sexual arousal of the female.

Female sexual arousal is enhanced by stimulation of the vulva, such as touching or caressing the clitoris.

Hand held or other external devices that stimulate the clitoris are well-known. For example U.S. Pat. No. 7,081, 087B2 discloses a sexual aid that vibrates. There has been proposed a device for treating FSD that applies a vacuum or suction to the clitoris. This will create a negative pressure that promotes the engorgement of the clitoris with blood (Hovland Claire, U.S. Pat. No. 6,464,653B1).

The local administration of prostaglandins to the female genetalia in order to treat FSD has been described in U.S. Pat. No. 6,486,207.

The implantation of an electrode that stimulates the peripheral nerves of the vulva has been described (US 2008/0103544).

SUMMARY OF THE INVENTION

It is an object of the present invention to obviate at least some of the disadvantages in the prior art and provide a new strategy for treating female sexual dysfunction by positively affecting sexual stimuli and orgasm.

One characteristic of the invention is to enable the patient to enhance the patient's own response to sexual stimuli from the partner.

One advantage is that the likelihood to get orgasm will increase by the stimulation device.

Another advantage is that the sexual response to sexual stimuli will increase.

The proposed device is implanted. An advantage with the implantation of a stimulating device is that it is always at hand and can conveniently be switched on before sexual intercourse. Hand held devices are more likely to cause embarrassment.

In a first aspect there is provided an apparatus for treating a sexual dysfunctional female patient, comprising an implanted at least one stimulation device adapted to stimulate at least a part of the sexually responsive tissue of the vulva or the wall of the vagina of the patient by movement of said stimulation device and contact between said stimulation device and at least one area of the sexually responsive tissue or the wall of the vagina.

In a second aspect there is provided at least one operation device adapted to operate said at least one stimulation device. The operation device may be an integrated part of the stimulation device or the stimulation and operation device may be the same and one unit. The at least one operation device may be also implanted at a distance from the at least one stimulating device.

Further embodiments comprise that the at least one stimulating device is adapted to be implanted in the region of the sexually responsive tissue of the vulva or the wall of the vagina, wherein the at least one stimulating device is adapted to create movement preferable with a frequency from 0.1 to 10,000 Hz, and wherein the at least one stimulating device is adapted to create movement preferable with an amplitude of from 0.01 to 30 mm.

The apparatus may further comprise a control device for manually controlling the at least one stimulating device from outside the patients body, and may further comprise a control device for controlling the intensity of the stimulation device.

Alternatively the apparatus may comprise a control device and at least one sensor adapted to detect a physiological parameter of the patient and/or a functional parameter of the apparatus, wherein said control device comprises a control unit adapted to automatically control the at least one stimulating device based on input from said at least one sensor.

The operation device may comprise many different embodiments such as; an electromagnetic device, wherein the movement is achieved by said electromagnetic device, an electric motor, wherein the movement is achieved by said electric motor, a hydraulic device, wherein the movement is achieved by said hydraulic device, a mechanical device, wherein the movement is achieved by said mechanical device, a motor, wherein the movement is achieved by said motor.

In a preferred embodiment, the system comprises at least one switch implantable in the patient for manually and non-invasively controlling the apparatus In another preferred embodiment, the system comprises a wireless remote control for non-invasively controlling the apparatus.

In a preferred embodiment, the system comprises a hydraulic operation device for operating the apparatus.

In one embodiment, the system comprises comprising a motor or a pump for operating the apparatus.

There are also included a method operating and using said stimulation device. In a first aspect there is provided an operation method using the apparatus comprising the steps of: creating an opening in the skin or vaginal wall of the female patient, dissecting an one area of the sexually responsive tissue, placing the stimulation device within said area, adapted to postoperatively stimulate said sexually responsive tissue on patient command.

Further steps may include placing an operation device and a power source within the body.

The step of placing a stimulation device may comprise placing an integrated unit comprising the stimulation device and an operation device in the same integrated unit.

The step of placing a power source may comprise placing a control unit and a rechargeable battery remote from said sexually responsive tissue.

The operation method preferable includes controlling said stimulation device post-operatively and non-invasively from outside the body.

In a second aspect there is provided a laparoscopic operation method, wherein the step of creating an opening in the skin or vaginal wall of the female patient comprising: inserting a tube or needle into the patients body, filling the tube or needle with a gas and thereby expanding a cavity within the female patients body, inserting at least two laparoscopic trocars into said cavity, inserting at least one camera trough at least one laparoscopic trocar, inserting at least one dissecting tool through at least one laparoscopic trocar, Further aspects and embodiments are defined in the appended claims, which are specifically incorporated herein by reference.

Definitions

Before the invention is disclosed and described in detail, it is to be understood that this invention is not limited to particular surgical steps, configurations, method steps, substrates, and materials disclosed herein as such surgical steps, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

The term "contact" refers to: union or junction of surfaces, including but not limited to: touching, contact, stroking and poking.

The term "movement" refers to: changing of place or position or posture, including but not limited to: vibration, oscillation, kneading, rotation, alternating expansion and contraction.

The term "Sexually responsive tissue of the vulva" refers to: the clitoris, labia minor, labia major, the corpora cavernosa and the vestibule.

The term "in the region of" refers to: in or close to.

The term "female erectile tissue" as used throughout the description and the claims denotes i) tissue of the female sexual organs that before or during sexual intercourse are filled with blood including the corpora cavernosa of the clitoris and the vestibular bulbs, ii) extensions of said tissue, including blood vessels and the surrounding tissues.

DETAILED DESCRIPTION OF THE INVENTION

In a first aspect there is provided an apparatus for treating a sexual dysfunctional female patient, comprising an implanted at least one stimulation device adapted to stimulate at least a part of the sexually responsive tissue of the vulva or the wall of the vagina of the patient by movement of said stimulation device and contact between said stimulation device and at least one area of the sexually responsive tissue.

In various embodiments the apparatus stimulates selected parts of the female genitalia. Thus in one embodiment the apparatus stimulates the sexually responsive tissue of the vulva.

In one embodiment the apparatus stimulates the wall of the vagina.

In one embodiment the apparatus stimulates one or more of the clitoris, the labia major, the labia minor, the vestibule and the corpora cavernosa.

In a main embodiment there is provided an apparatus comprising at least one operation device adapted to operate said at least one stimulation device, where the at least one stimulating device is adapted to be implanted in the region of the sexually responsive tissue of the vulva or the wall of the vagina. The stimulating device is adapted to move with a frequency from 0.1 to 10,000 Hz and with an amplitude of from 0.01 to 30 mm. In one embodiment the at least one stimulating device is adapted to create movements along more than one axis.

In one embodiment the invention further comprises a control device for manually controlling the at least one stimulating device from outside the patients body. The control device controls the intensity of movement of the stimulation device. The control device may independently control amplitude and frequency of the movement in the two different axes.

In another embodiment the apparatus comprises a control device and at least one sensor adapted to detect a physiological parameter of the patient and/or a functional parameter of the apparatus, wherein said control device comprises a control unit adapted to automatically control the at least one stimulating device based on input from said at least one sensor.

In another embodiment the at least one stimulating device is controlled by an endogenous signal.

In one embodiment the at least one operation device is adapted to be implanted at a distance from the at least one stimulating device.

In one embodiment there are at least two stimulating devices, adapted to be placed in the region of the sexually responsive tissue of the vulva or the wall of the vagina.

In one embodiment the operation device is an integrated part of the stimulation device or the stimulation device and operation device are the same and one unit.

The movement may be achieved by different means in different embodiments. Thus, operation device may comprise an electric motor, a hydraulic device, a mechanical device, or a magnetic device. The movement may also be achieved by a piezoelectric element, an eccentric mechanism, or an electromagnetic mechanism.

In one embodiment, the apparatus comprises at least one expandable prostheses adapted for implantation in female erectile tissue and adapted to be adjusted to temporarily achieve enlarged status of the female erectile tissue. The prostheses may be controlled and energized by the system in the same manner as the stimulation device.

In one embodiment the apparatus comprises at least one implantable reservoir, adapted to be implanted in the sexually responsive tissue of the vulva of the patient, wherein said at least one stimulation device is placed in said at least one reservoir.

In one embodiment, the stimulation device is adapted to be implanted in the region of the clitoris of the female patient.

In a second aspect there is provided a surgery method where an apparatus as described above is implanted in the patient.

A third aspect there is provided a system that comprises an apparatus as described above.

In one embodiment the system comprises at least one switch implantable in the patient for manually and non-invasively controlling the apparatus.

In one embodiment the system comprises a hydraulic device having an implantable hydraulic reservoir, which is hydraulically connected to the apparatus, wherein the apparatus is adapted to be non-invasively regulated by manually pressing the hydraulic reservoir.

In one embodiment the system comprises a wireless remote control for non-invasively controlling the apparatus. The wireless remote control may comprise at least one external signal transmitter and/or receiver, further comprising an internal signal receiver and/or transmitter implantable in the patient for receiving signals transmitted by the external signal transmitter or transmitting signals to the external signal receiver.

In one embodiment the wireless remote control transmits at least one wireless control signal for controlling the apparatus. The control signal may be different in different embodiments, for example an electric field, a magnetic field, or a combined electric and magnetic field In one embodiment the wireless control signal comprises a frequency, amplitude, or phase modulated signal or a combination thereof.

In one embodiment the wireless remote control transmits an electromagnetic carrier wave signal for carrying the control signal.

One embodiment comprises a wireless energy-transmission device for non-invasively energizing implantable energy consuming components of the apparatus or the system with wireless energy.

The wireless energy may comprise wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The signal may be an analogue signal, a digital signal, or a combination of an analogue and digital signal The wireless energy may be different in different embodiments, for example: an electric field, a magnetic field, or a combined electric and magnetic field.

In a main embodiment there is provided an implantable internal energy source for powering implantable energy consuming components of the apparatus.

In one embodiment there is provided an external energy source for transferring energy in a wireless mode, wherein the internal energy source is chargeable by the energy transferred in the wireless mode.

In one embodiment there is provided a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

One main embodiment further comprises a feedback device for sending feedback information from inside the patient's body to the outside thereof, the feedback information being related to at least one of a physiological parameter of the patient and a functional parameter related to the apparatus.

In one embodiment there is provided a sensor and/or a measuring device and an implantable internal control unit for controlling the apparatus in response to information being related to at least one of a physiological parameter of the patient sensed by the sensor or measured by the measuring device and a functional parameter related to the apparatus sensed by the sensor or measured by the measuring device. The physiological parameter may be a pressure or a motility movement.

In one embodiment there is provided an external data communicator and an implantable internal data communicator communicating with the external data communicator, wherein the internal communicator feeds data related to the apparatus or the patient to the external data communicator and/or the external data communicator feeds data to the internal data communicator.

In one embodiment there is provided a motor or a pump for operating the apparatus.

In one embodiment there is provided a hydraulic operation device for operating the apparatus.

In one embodiment there is provided an operation device for operating the apparatus, wherein the operation device comprises a servo designed to decrease the force needed for the operation device to operate the apparatus instead the operation device acting a longer way, increasing the time for a determined action.

In one embodiment there is provided an operation device for operating the apparatus, wherein the wireless energy is used in its wireless state to directly power the operation device to create kinetic energy for the operation of the apparatus, as the wireless energy is being transmitted by the energy-transmission device.

In one embodiment there is provided an energy-transforming device for transforming the wireless energy transmitted by the energy-transmission device from a first form into a second form energy.

In one embodiment the energy-transforming device directly powers implantable energy consuming components of the apparatus with the second form energy, as the energy-transforming device transforms the first form energy transmitted by the energy-transmission device into the second form energy.

In one embodiment the second form energy comprises at least one of a direct current, pulsating direct current and an alternating current.

In one embodiment there is provided an implantable accumulator, wherein the second form energy is used at least partly to charge the accumulator.

In one embodiment the energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

In one embodiment there are provided implantable electrical components including at least one voltage level guard and/or at least one constant current guard.

In one embodiment there is provided a control device for controlling the transmission of wireless energy from the energy-transmission device, and an implantable internal energy receiver for receiving the transmitted wireless energy, the internal energy receiver being connected to implantable energy consuming components of the apparatus for directly or indirectly supplying received energy thereto, the system further comprising a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

In one embodiment the determination device is adapted to detect a change in the energy balance, and the control device controls the transmission of wireless energy based on the detected energy balance change.

In one embodiment the determination device is adapted to detect a difference between energy received by the internal energy receiver and energy used for the implantable energy consuming components of the apparatus, and the control device controls the transmission of wireless energy based on the detected energy difference.

In one embodiment the energy-transmission device comprises a coil placed externally to the human body, further comprising an implantable energy receiver to be placed internally in the human body and an electric circuit connected to power the external coil with electrical pulses to transmit the wireless energy, the electrical pulses having leading and trailing edges, the electric circuit adapted to vary first time intervals between successive leading and trailing edges and/or second time intervals between successive trailing and leading edges of the electrical pulses to vary the power of the transmitted wireless energy, the energy receiver receiving the transmitted wireless energy having a varied power.

In one embodiment the electric circuit is adapted to deliver the electrical pulses to remain unchanged except varying the first and/or second time intervals.

In one embodiment the electric circuit has a time constant and is adapted to vary the first and second time intervals only in the range of the first time constant, so that when the lengths of the first and/or second time intervals are varied, the transmitted power over the coil is varied.

In one embodiment there is provided a system comprising an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off.

In one embodiment there is a an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil, wherein the external second coil of the energy transmitter transmits wireless energy which is received by the first coil of the energy receiver, the system further comprising a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils.

In one embodiment the transmitted energy may be regulated depending on the obtained coupling factor.

In one embodiment there is provided a system wherein the external second coil is adapted to be moved in relation to the internal first coil to establish the optimal placement of the second coil, in which the coupling factor is maximized.

In one embodiment there is provided a system wherein the external second coil is adapted to calibrate the amount of transferred energy to achieve the feedback information in the determination device, before the coupling factor is maximized.

In a third aspect there is provided an operation method using an apparatus or system according to the above further comprising the steps of: a) creating an opening in the skin or vaginal wall of the female patient, b) dissecting an one area of the sexually responsive tissue, c) placing the stimulation device within said area, adapted to postoperatively stimulate said sexually responsive tissue on patient command.

In one embodiment there is provided an operation method comprising the step of placing an operation device and a power source within the body.

In one embodiment the operation method comprises placing a stimulation device comprising placing an integrated unit comprising the stimulation device and an operation device in the same integrated unit.

In one embodiment the operation method comprises placing a power source comprising, placing a control unit and a rechargeable battery remote from said sexually responsive tissue.

In one embodiment the operation method comprises controlling said stimulation device post-operatively and non-invasively from outside the body.

In one embodiment the operation method comprises the step of creating an opening in the skin or vaginal wall of the female patient comprising, a) inserting a tube or needle into the patients body, b) filling the tube or needle with a gas and thereby expanding a cavity within the female patients body, c) inserting at least two laparoscopic trocars into said cavity, d) inserting at least one camera trough at least one laparoscopic trocar, e) inserting at least one dissecting tool through at least one laparoscopic trocar,

BRIEF DESCRIPTION OF THE DRAWINGS

The present invention will now be described in more detail by way of non-limiting examples and with reference to the accompanying drawings, in which:

FIGS. 2-16 schematically show various embodiments of the system for wirelessly powering the apparatus shown in FIG. 1.

FIGS. 21-27C show various ways of arranging hydraulic or pneumatic powering of an apparatus implanted in a patient.

DETAILED DESCRIPTION OF PREFERRED EMBODIMENTS

Figure 1A:
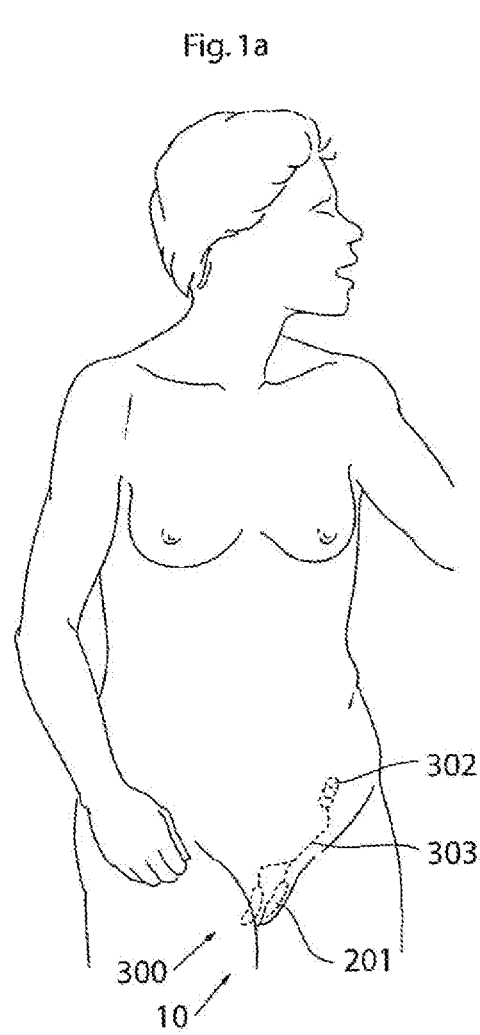
FIG. 1a-g illustrates an apparatus and a system for treating female sexual dysfunction, wherein the system includes an apparatus of the invention implanted in a patient.

FIG. 1a illustrates a system 300 for treating a female patient suffering from FSD comprising an apparatus 10, comprising two stimulation devices 201, of the present invention placed in the abdomen of a patient. An implanted operation device 302 is adapted to supply energy consuming components of the apparatus with energy via a power supply line 303.

Figure 1B:
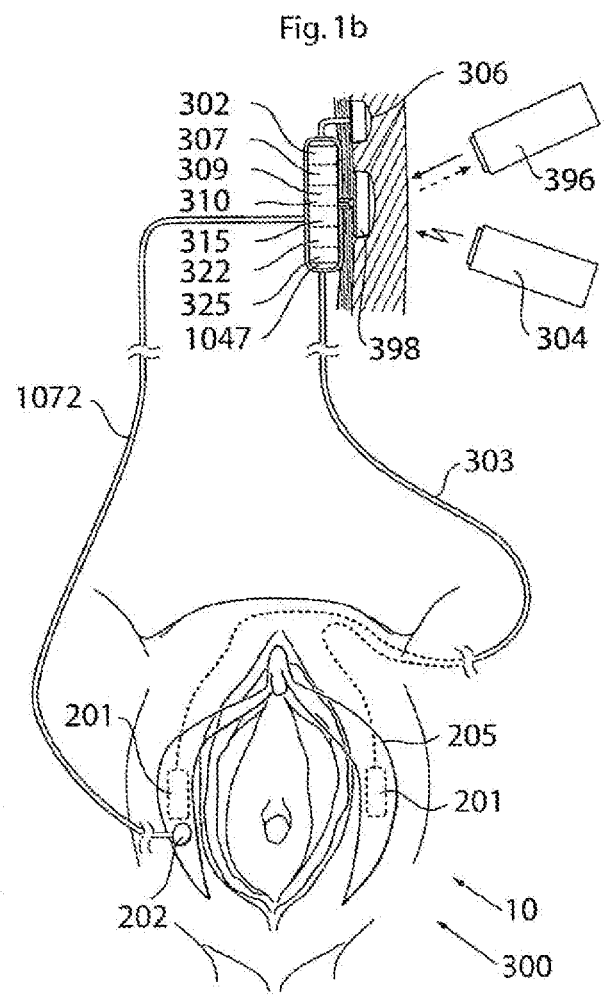

FIG. 1b shows the apparatus 10 and system 300 in more detail. The apparatus 10 comprises two stimulation devices 201. The apparatus 10 is implanted and in contact with the sexually responsive tissue of the vulva 205 of the patient. An implanted operation device 302 is adapted to supply energy consuming components of the apparatus with energy via a power supply line 303.

An external energy-transmission device 304 for non-invasively energizing the apparatus 10 transmits energy by at least one wireless energy signal. The implanted energy-transforming device 398 transforms energy from the wireless energy signal into electric energy which is supplied via the power supply line 303.

The system 300 can be controlled with a remote control 396. Also a subcutaneous control switch 306 can be used to control the apparatus. In one embodiment a sensor 202 measures at least one physiological or functional parameter. The location of the sensor 202 is adapted to the circumstances, e.g. which parameter that should be measured. The sensor 202 may e.g. be connected to the energy-transforming device 398 or the control unit 315 via a communication line 1072 that also may supply power to the sensor 202.

The operation device 302 may comprise at least one item selected from the group consisting of; a control unit 315, a battery 322, a sensor 325, a motor 307, a pump 309, a reservoir 310. The item 1047 may be an injection port. The items are selected depending on the circumstances, e.g. if the apparatus is electrically, hydraulically, pneumatically or mechanically operated.

If a non-rechargeable battery is used the energy-transforming device 398 may be omitted but the items 307, 309, 310, 315, 322, 325, and 1047 may be used as suitable, and be connected to the apparatus 10 and sensor 202 as suitable. If e.g. the apparatus 10 is hydraulically operated it may e.g. be suitable to use a control unit 315, an injection port 1047, a pump 309 and/or a reservoir 310.

In general, any item, or combinations of items, described and suited therefore, may be connected to the apparatus 10 via the power supply line 303. The actual item, or combinations of items, are chosen depending on the circumstances, e.g. if the apparatus 10 is electrically, hydraulically, pneumatically or mechanically operated.

If e.g. the apparatus 10 is mechanically operated it may be connected to a motor 307 via the power supply line 303 which in this case may be a wire or bowden cable. A control unit 315 may be connected to the motor 307.

If e.g. the apparatus 10 is electrically operated it may be suitable to connect it to a source of electrical energy 322 via the power supply line 303 which in this case may be an electrical conduit. A control unit 315 may be connected to the source of electrical energy 322.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 398 is provided for transforming wireless energy of a first form transmitted by the energy-transmission device 304 into energy of a second form, which typically is different from the energy of the first form. The implanted apparatus 10 is operable in response to the energy of the second form. The energy-transforming device 398 may directly power the apparatus with the second form energy, as the energy-transforming device 398 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 398 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 398 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Figure 1C:
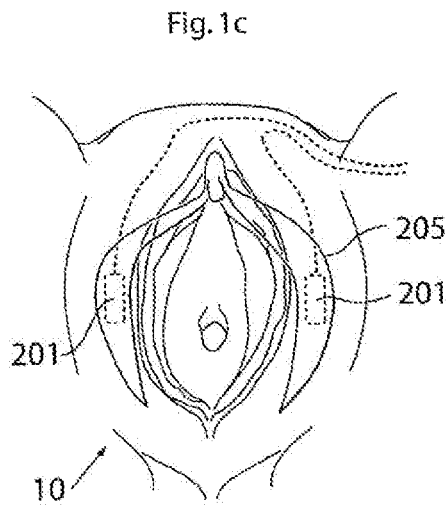

FIG. 1c illustrates an apparatus comprising two stimulation devices 201, implanted in the sexually responsive tissue of the vulva 205 of the patient.

Figure 1D:
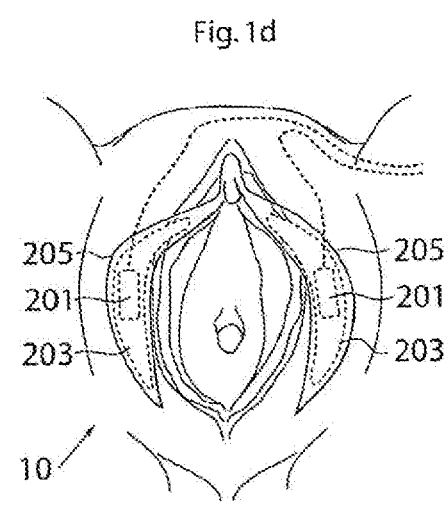

FIG. 1d illustrates an apparatus 10 implanted in the sexually responsive tissue of the vulva 205 of the patient. Here the apparatus comprising the stimulation device 201 and the stimulation device is inside a prosthesis 203. The prosthesis may be expandable to temporarily achieve enlarged status of the female erectile tissue. The prostheses is controlled and energized by the system 300 in the same manner as the stimulation device.

Figure 1E:
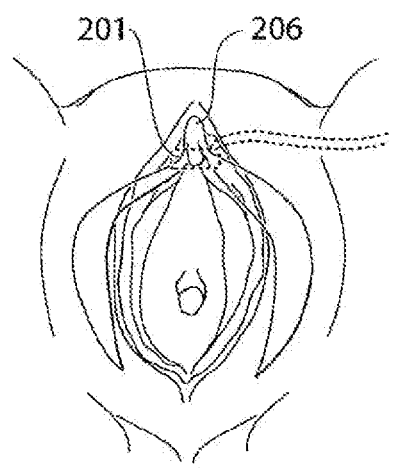

FIG. 1e illustrates the stimulation device 201 implanted so that it can stimulate the clitoris 206 of the patient.

Figure 1F:
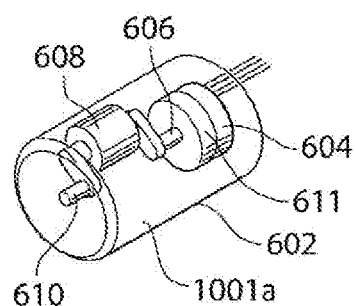

FIG. 1f schematically shows one exemplary embodiment, where an eccentric mechanism is used for achieving vibration or movement of the device. A motor device 201a, of the stimulation device 201, said motor device 201a, comprising an outer shell 602, a motor 604, a first motor axis 606, an eccentric element 608 eccentrically mounted to the first motor axis 606, a second axis 610 which suitably is supported by a bearing mounted to the outer shell 602. The motor device 1001a may comprise a gear box 611 that transforms the speed of rotation of the motor to a suitable speed.

Figure 1G:
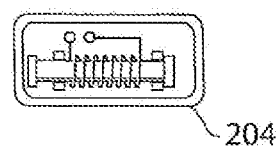

FIG. 1g illustrates an electromagnetic device 204 which is one mean of making the stimulation device 201 move.

FIG. 2 illustrates the system 300 of FIG. 1 in the form of a more generalized block diagram showing the apparatus 10, the energy-transforming device 398 powering the apparatus 10 via power supply line 303, and the external energy-transmission device 304, The patient's skin 305, generally shown by a vertical line, separates the interior of the patient to the right of the line from the exterior to the left of the line.

FIG. 3 shows an embodiment of the invention identical to that of FIG. 2, except that a reversing device in the form of an electric switch 306 operable for example by polarized energy also is implanted in the patient for reversing the apparatus 10. When the switch is operated by polarized energy the wireless remote control of the external energy-transmission device 304 transmits a wireless signal that carries polarized energy and the implanted energy-transforming device 398 transforms the wireless polarized energy into a polarized current for operating the electric switch 306. When the polarity of the current is shifted by the implanted energy-transforming device 398 the electric switch 306 reverses the function performed by the apparatus 10.

FIG. 4 shows an embodiment of the invention identical to that of FIG. 2, except that a motor 307 implanted in the patient for operating the apparatus 10 is provided between the implanted energy-transforming device 398 and the apparatus 10. The motor 307 is powered with energy from the implanted energy-transforming device 398, as the remote control of the external energy-transmission device 304 transmits a wireless signal to the receiver of the implanted energy-transforming device 398.

FIG. 5 shows an embodiment of the invention identical to that of FIG. 2, except that it also comprises an operation device is in the form of an assembly 308 including a motor/pump unit 309 and a fluid reservoir 310 is implanted in the patient. In this case the apparatus 10 is hydraulically operated, i.e. hydraulic fluid is pumped by the motor/pump unit 309 from the fluid reservoir 310 through a conduit 311 to the apparatus 10 to operate the apparatus, and hydraulic fluid is pumped by the motor/pump unit 309 back from the apparatus 10 to the fluid reservoir 310 to return the apparatus to a starting position. The implanted energy-transforming device 398 transforms wireless energy into a current, for example a polarized current, for powering the motor/pump unit 309 via an electric power supply line 312.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 398 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 6:
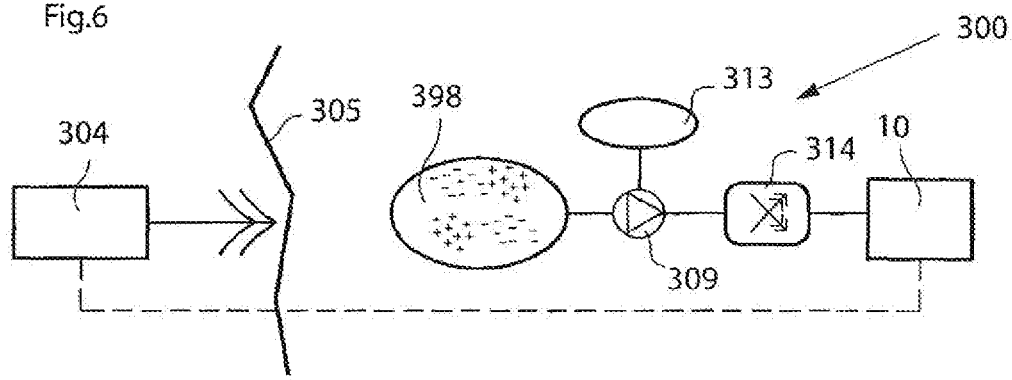

FIG. 6 shows an embodiment of the invention comprising the external energy-transmission device 304 with its wireless remote control, the apparatus 10, in this case hydraulically operated, and the implanted energy-transforming device 398, and further comprising a hydraulic fluid reservoir 313, a motor/pump unit 309 and an reversing device in the form of a hydraulic valve shifting device 314, all implanted in the patient. Of course the hydraulic operation could easily be performed by just changing the pumping direction and the hydraulic valve may therefore be omitted.

The remote control may be a device separated from the external energy-transmission device or included in the same. The motor of the motor/pump unit 309 is an electric motor. In response to a control signal from the wireless remote control of the external energy-transmission device 304, the implanted energy-transforming device 398 powers the motor/pump unit 309 with energy from the energy carried by the control signal, whereby the motor/pump unit 309 distributes hydraulic fluid between the hydraulic fluid reservoir 313 and the apparatus 10. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to the apparatus 10 to operate the apparatus, and another opposite direction in which the fluid is pumped by the motor/pump unit 309 back from the apparatus 10 to the hydraulic fluid reservoir 313 to return the apparatus to a starting position.

Figure 7:
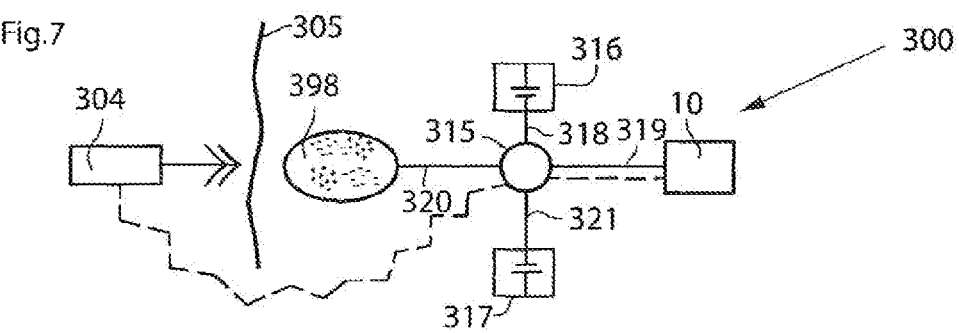

FIG. 7 shows an embodiment of the invention comprising the external energy-transmission device 304 with its wireless remote control, the apparatus 10, the implanted energy-transforming device 398, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 398 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 398 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physiological parameter of the patient or any functional parameter of the system.

In accordance with an alternative, the capacitor 317 in the embodiment of FIG. 7 may be omitted. In accordance with another alternative, the accumulator 316 in this embodiment may be omitted.

Figure 8:
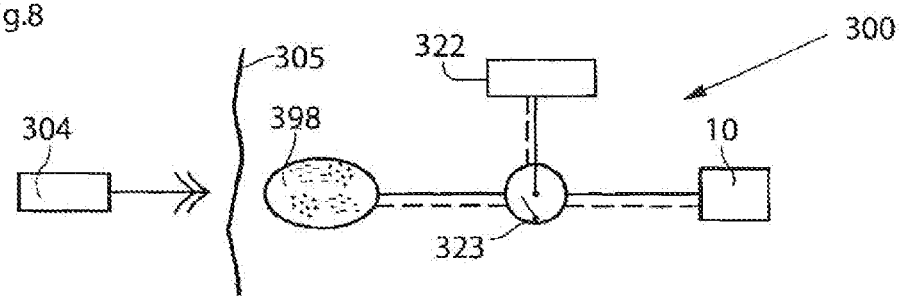

FIG. 8 shows an embodiment of the invention identical to that of FIG. 2, except that a battery 322 for supplying energy for the operation of the apparatus 10 and an electric switch 323 for switching the operation of the apparatus 10 are also implanted in the patient. The electric switch 323 may be controlled by the remote control and may also be operated by the energy supplied by the implanted energy-transforming device 398 to switch from an off mode, in which the battery 322 is not in use, to an on mode, in which the battery 322 supplies energy for the operation of the apparatus 10.

Figure 9:
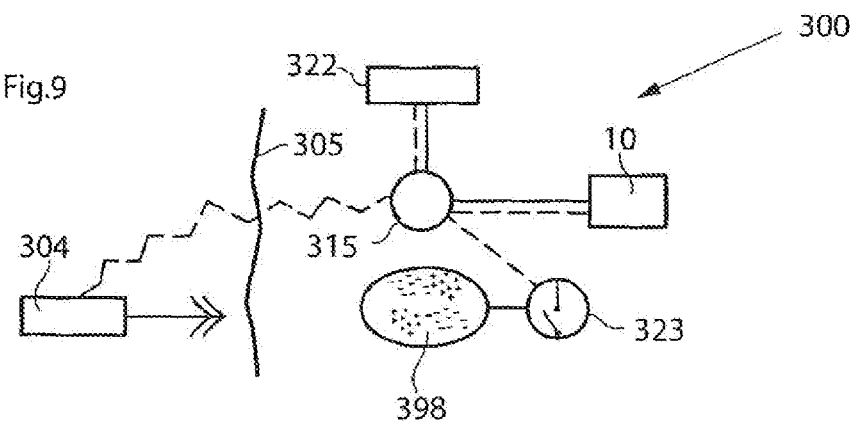

FIG. 9 shows an embodiment of the invention identical to that of FIG. 8, except that an internal control unit 315 controllable by the wireless remote control of the external energy-transmission device 304 also is implanted in the patient. In this case, the electric switch 323 is operated by the energy supplied by the implanted energy-transforming device 398 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

Figure 10:
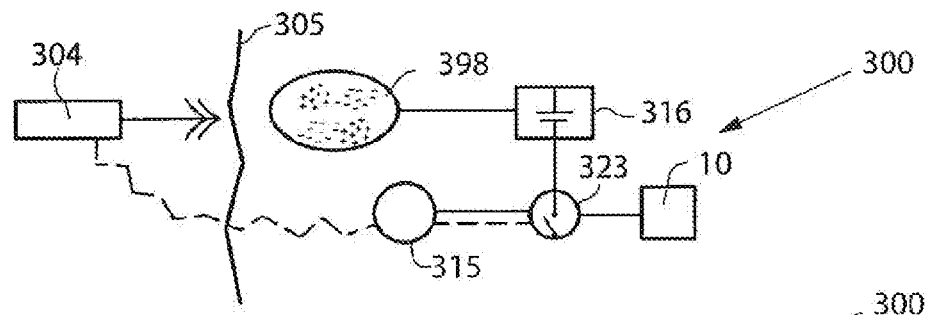

FIG. 10 shows an embodiment of the invention identical to that of FIG. 9, except that an accumulator 316 is substituted for the battery 322 and the implanted components are interconnected differently. In this case, the accumulator 316 stores energy from the implanted energy-transforming device 398. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 11:
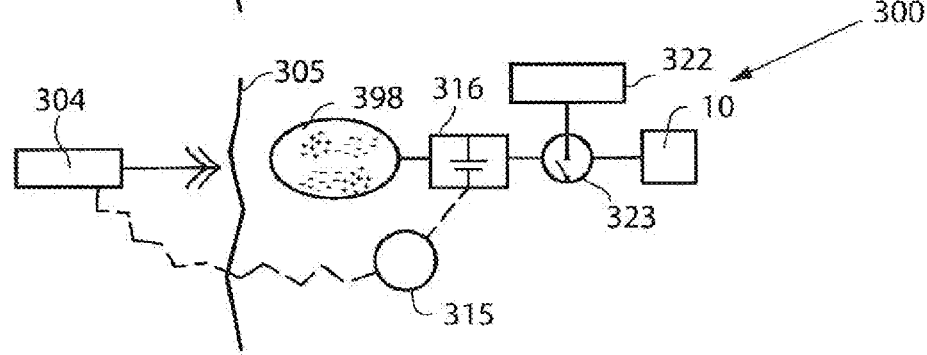

FIG. 11 shows an embodiment of the invention identical to that of FIG. 10, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

Figure 12:
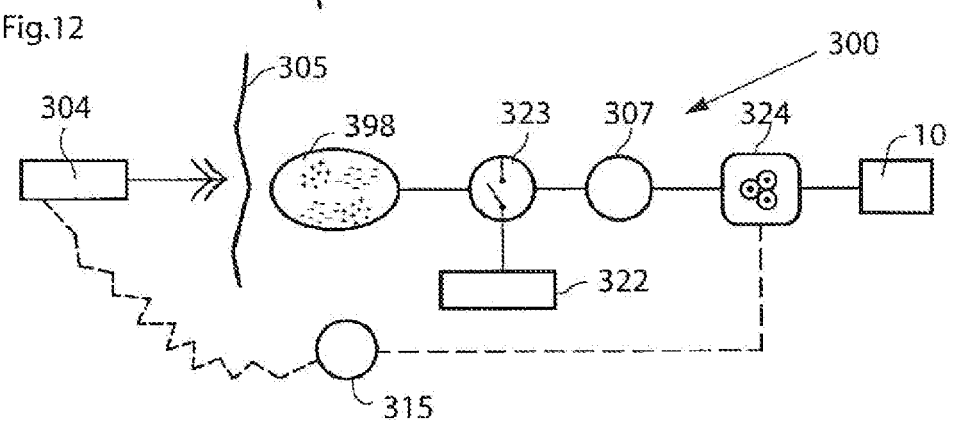

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit. FIG. 12 shows an embodiment of the invention identical to that of FIG. 8, except that a motor 307, a mechanical reversing device in the form of a gear box 324, and an internal control unit 315 for controlling the gear box 324 also are implanted in the patient. The internal control unit 315 controls the gear box 324 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 13:
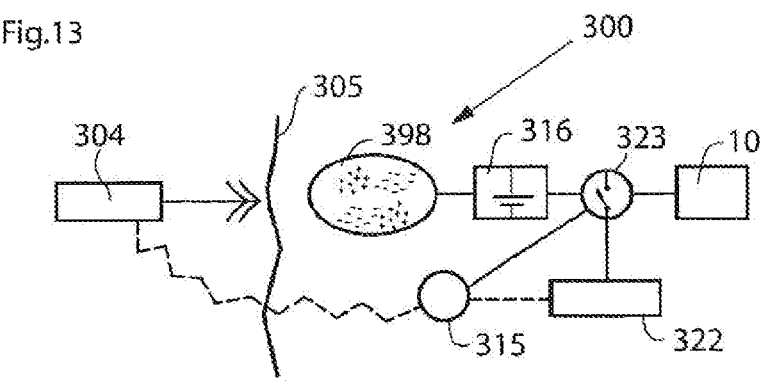
Figure 19:
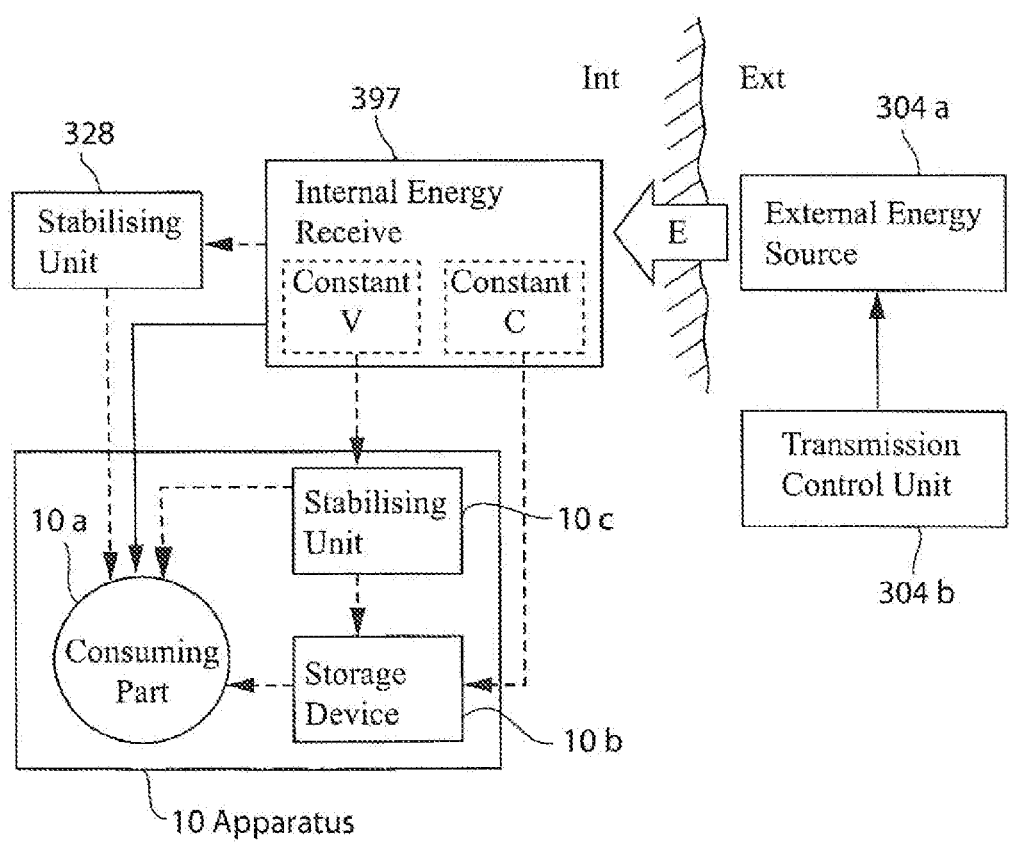
FIG. 19 is a more detailed block diagram of an arrangement for controlling the transmission of wireless energy used for the operation of the apparatus shown in FIG. 1.

FIG. 13 shows an embodiment of the invention identical to that of FIG. 19 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of the apparatus 10.

Figure 14:
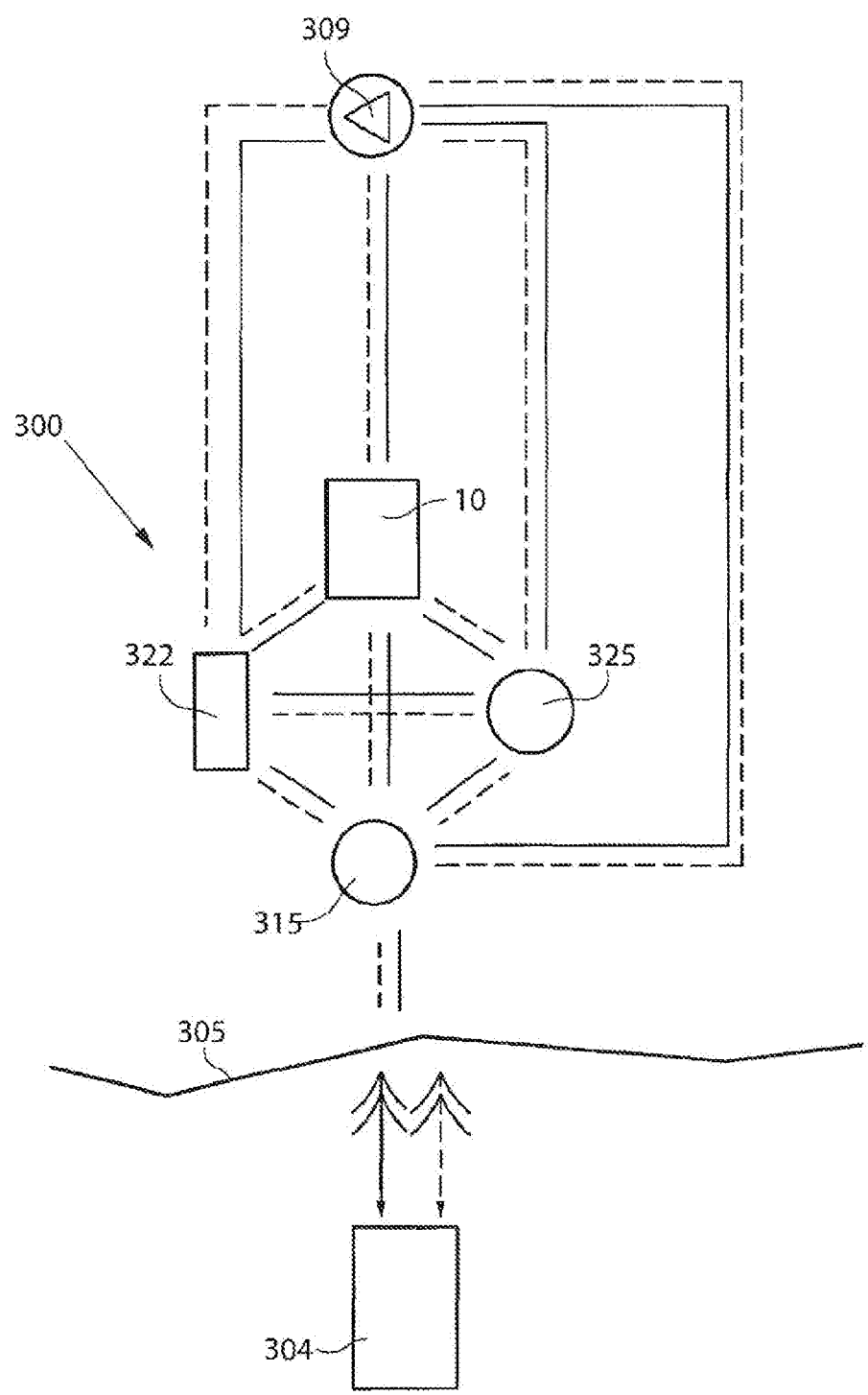

FIG. 14 schematically shows conceivable combinations of implanted components of the apparatus for achieving various communication options. Basically, there are the apparatus 10, the internal control unit 315, motor or pump unit 309, and the external energy-transmission device 304 including the external wireless remote control. As already described above the wireless remote control transmits a control signal which is received by the internal control unit 315, which in turn controls the various implanted components of the apparatus.

A feedback device, preferably comprising a sensor or measuring device 325, may be implanted in the patient for sensing a physiological parameter of the patient. The physiological parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physiological parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 315, or alternatively the external wireless remote control of the external energy-transmission device 304, may control the apparatus 10 in response to signals from the sensor 325. A transceiver may be combined with the sensor 325 for sending information on the sensed physiological parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof.

Where the motor/pump unit 309 and battery 322 for powering the motor/pump unit 309 are implanted, information related to the charging of the battery 322 may be fed back. To be more precise, when charging a battery or accumulator with energy feed back information related to said charging process is sent and the energy supply is changed accordingly.

Figure 15:
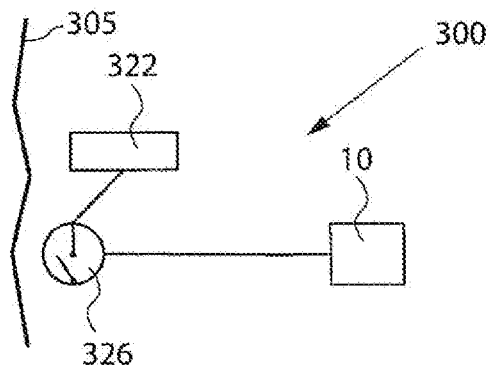

FIG. 15 shows an alternative embodiment wherein the apparatus 10 is regulated from outside the patient's body. The system 300 comprises a battery 322 connected to the apparatus 10 via a subcutaneous electric switch 326. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 16:
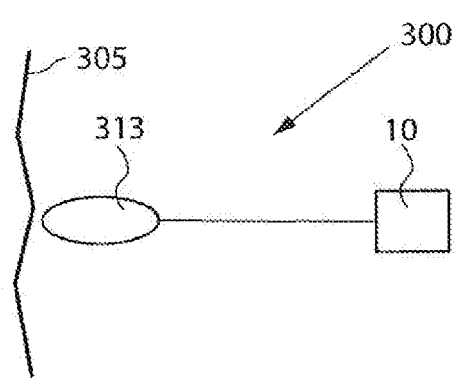

FIG. 16 shows an alternative embodiment, wherein the system 300 comprises a hydraulic fluid reservoir 313 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 17:
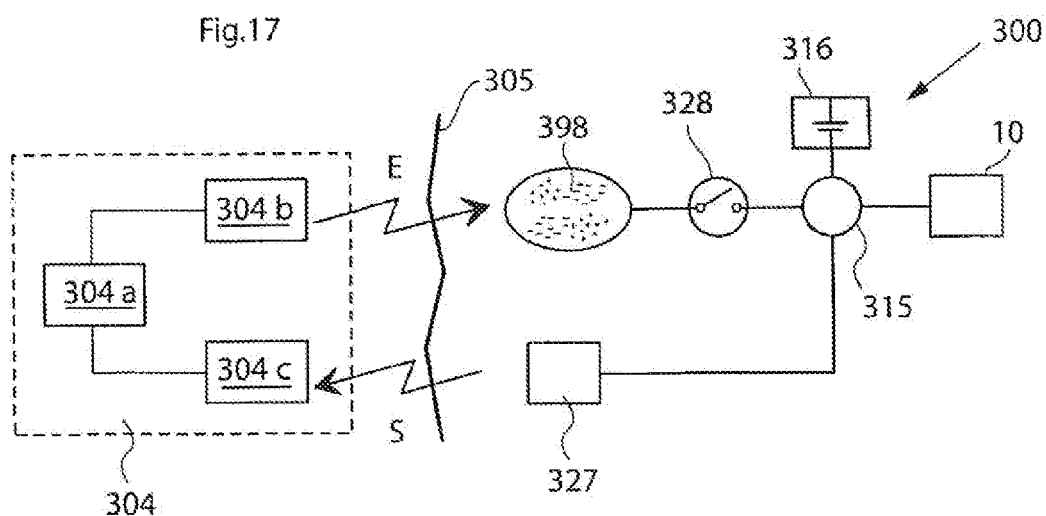
FIG. 17 is a schematic block diagram illustrating an arrangement for supplying an accurate amount of energy used for the operation of the apparatus shown in FIG. 1.

FIG. 17 schematically illustrates an arrangement of the system that is capable of sending information from inside the patient's body to the outside thereof to give feedback information related to at least one functional parameter of the apparatus or system, or related to a physiological parameter of the patient, in order to supply an accurate amount of energy to an implanted internal energy receiver 398 connected to implanted energy consuming components of the apparatus 10. Such an energy receiver 398 may include an energy source and/or an energy-transforming device. Briefly described, wireless energy is transmitted from an external energy source 304a located outside the patient and is received by the internal energy receiver 398 located inside the patient. The internal energy receiver is adapted to directly or indirectly supply received energy to the energy consuming components of the apparatus 10. An energy balance is determined between the energy received by the internal energy receiver 398 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 17 the patient's skin is indicated by a vertical line 305. Here, the energy receiver comprises an energy-transforming device 398 located inside the patient, preferably just beneath the patient's skin 305. Generally speaking, the implanted energy-transforming device 398 may be placed in the abdomen, thorax, muscle fascia (e.g. in the abdominal wall), subcutaneously, or at any other suitable location. The implanted energy-transforming device 398 is adapted to receive wireless energy E transmitted from the external energy source 304a provided in an external energy-transmission device 304 located outside the patient's skin 305 in the vicinity of the implanted energy-transforming device 398.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 398. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external energy source 304*a* based on the determined energy balance to regulate the amount of transferred energy. In order to transfer the correct amount of energy, the energy balance and the required amount of energy is determined by means of a determination device including an implanted internal control unit 315 connected to the apparatus 10.

The internal control unit 315 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physiological parameters of the patient and functional parameters of the device are described elsewhere.

Furthermore, an energy source in the form of an accumulator 316 may optionally be connected to the implanted energy-transforming device 398 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 398, i.e. not too little or too much.

The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304*c* connected to the external control unit 304*b*. The amount of energy transmitted from the external energy source 304*a* may then be regulated in response to the received control signal.

Alternatively, the determination device may include the external control unit 304*b*. In this alternative, sensor measurements can be transmitted directly to the external control unit 304*b* wherein the energy balance and/or the currently required amount of energy can be determined by the external control unit 304*b*, thus integrating the above-described function of the internal control unit 315 in the external control unit 304*b*. In that case, the internal control unit 315 can be omitted and the sensor measurements are supplied directly to the internal signal transmitter 327 which sends the measurements over to the external signal receiver 304*c* and the external control unit 304*b*. The energy balance and the currently required amount of energy can then be determined by the external control unit 304*b* based on those sensor measurements.

Hence, the present solution according to the arrangement of FIG. 17 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304*c* may be implemented as separate units using suitable signal transfer means, such as radio, IR (Infrared) or ultrasonic signals. Alternatively, the internal signal transmitter 327 and the external signal receiver 304*c* may be integrated in the implanted energy-transforming device 398 and the external energy source 304*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 328 is either separate and controlled by the internal control unit 315, or integrated in the internal control unit 315. It should be understood that the switch 328 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 17 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics. This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factors information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils. The transmitted energy may be regulated depending on the obtained coupling factor.

Figure 18:
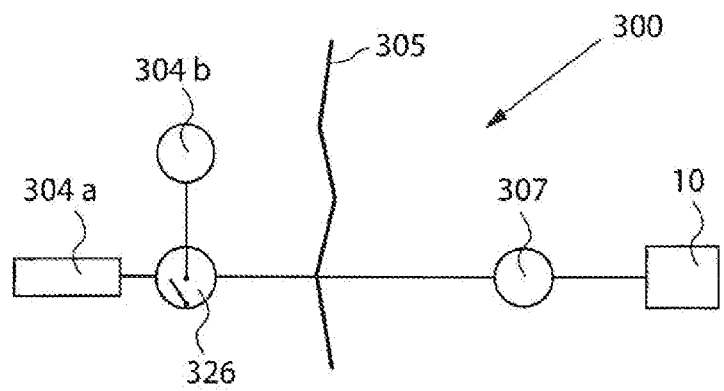
FIG. 18 schematically shows an embodiment of the system, in which the apparatus is operated with wire bound energy.

With reference to FIG. 18, although wireless transfer of energy for operating the apparatus has been described above to enable non-invasive operation, it will be appreciated that the apparatus can be operated with wire bound energy as well. Such an example is shown in FIG. 18, wherein an external switch 326 is interconnected between the external energy source 304a and an operation device, such as an electric motor 307 operating the apparatus 10. An external control unit 304b controls the operation of the external switch 326 to effect proper operation of the apparatus 10.

FIG. 19 illustrates different embodiments for how received energy can be supplied to and used by the apparatus 10. Similar to the example of FIG. 17, an internal energy receiver 397 receives wireless energy E from an external energy source 304a which is controlled by a transmission control unit 304b. The internal energy receiver 397 may comprise a constant voltage circuit, indicated as a dashed box "constant V" in the figure, for supplying energy at constant voltage to the apparatus 10. The internal energy receiver 397 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 397. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 397. Thus, the energy may be supplied in a fluctuating manner such that it may be necessary to stabilize the energy before consumed or stored.

The energy supplied from the internal energy receiver 397 may further be accumulated and/or stabilized by a separate energy stabilizing unit 10c located outside the apparatus 10, before being consumed and/or stored by the apparatus 10. Alternatively, the energy stabilizing unit 10c may be integrated in the internal energy receiver 397. In either case, the energy stabilizing unit 10c may comprise a constant voltage circuit and/or a constant current circuit.

It should be noted that FIG. 17 and FIG. 19 illustrate some possible but non-limiting implementation options regarding how the various shown functional components and elements can be arranged and connected to each other. However, the skilled person will readily appreciate that many variations and modifications can be made within the scope of the present invention.

Figure 20:
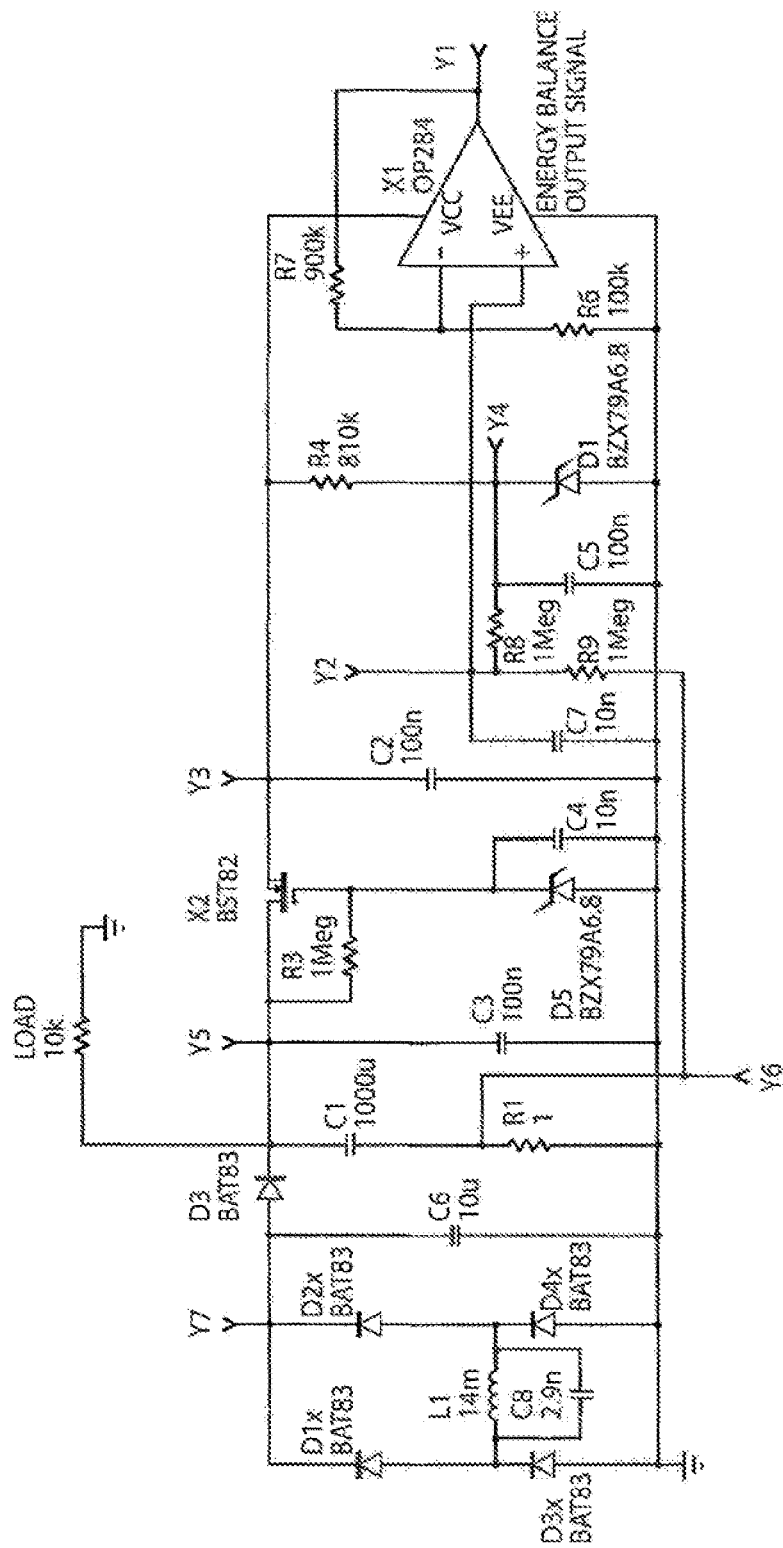
FIG. 20 is a circuit for the arrangement shown in FIG. 19, according to a possible implementation example.

FIG. 20 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such change takes place. If the amount of received energy is lower than the energy used by the implant, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 20 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 3; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 20 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 3 could be incorporated in any of the embodiments of FIGS. 6-12, the hydraulic valve shifting device 314 of FIG. 6 could be incorporated in the embodiment of FIG. 5, and the gear box 324 could be incorporated in the embodiment of FIG. 4. Please observe that the switch simply could mean any electronic circuit or component.

The embodiments described in connection with FIGS. 17, 19 and 20 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physiological parameters of the medical device and/or physiological parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physiological parameters of the apparatus and/or physiological parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 21-24 show in more detail block diagrams of four different ways of hydraulically or pneumatically powering an implanted apparatus according to the invention.

Figure 21:
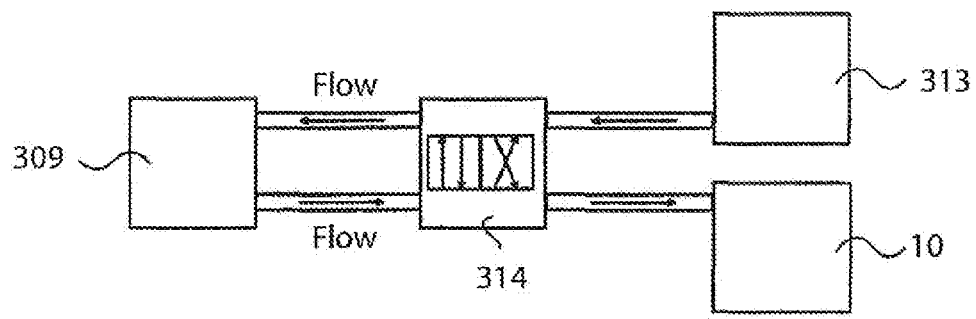

FIG. 21 shows a system as described above with. The system comprises an implanted apparatus 10 and further a separate regulation reservoir 313, a one way pump 309 and an alternate valve 314.

Figure 22:

FIG. 22 shows the apparatus 10 and a fluid reservoir 313. By moving the wall of the regulation reservoir or changing the size of the same in any other different way, the adjustment of the apparatus may be performed without any valve, just free passage of fluid any time by moving the reservoir wall.

Figure 23:
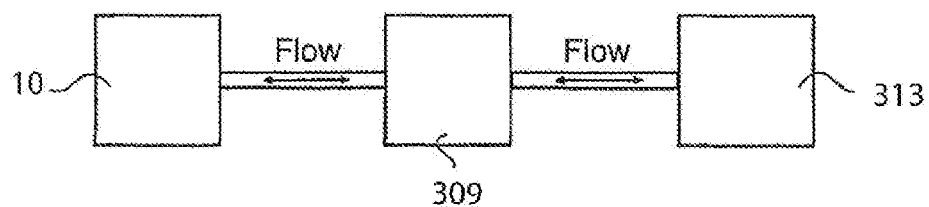
Figure 26:
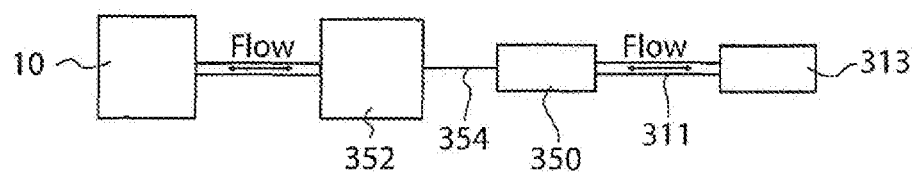

FIG. 23 shows the apparatus 10, a two way pump 309 and the regulation reservoir 313.

FIG. 24 shows a block diagram of a reversed servo system with a first closed system controlling a second closed system. The servo system comprises a regulation reservoir 313 and a servo reservoir 350. The servo reservoir 350 mechanically controls an implanted apparatus 10 via a mechanical interconnection 354. The apparatus has an expandable/contactable cavity. This cavity is preferably expanded or contracted by supplying hydraulic fluid from the larger adjustable reservoir 352 in fluid connection with the apparatus 10. Alternatively, the cavity contains compressible gas, which can be compressed and expanded under the control of the servo reservoir 350.

The servo reservoir 350 can also be part of the apparatus itself.

In one embodiment, the regulation reservoir is placed subcutaneous under the patient's skin and is operated by pushing the outer surface thereof by means of a finger. This system is illustrated in FIGS. 25a-c. In FIG. 25a, a flexible subcutaneous regulation reservoir 313 is shown connected to a bulge shaped servo reservoir 350 by means of a conduit 311. This bellow shaped servo reservoir 350 is comprised in a flexible apparatus 10. In the state shown in FIG. 25a, the servo reservoir 350 contains a minimum of fluid and most fluid is found in the regulation reservoir 313. Due to the mechanical interconnection between the servo reservoir 350 and the apparatus 10, the outer shape of the apparatus 10 is contracted, i.e., it occupies less than its maximum volume. This maximum volume is shown with dashed lines in the figure.

FIG. 25b shows a state wherein a user, such as the patient in with the apparatus is implanted, presses the regulation reservoir 313 so that fluid contained therein is brought to flow through the conduit 311 and into the servo reservoir 350, which, thanks to its bellow shape, expands longitudinally. This expansion in turn expands the apparatus 10 so that it occupies its maximum volume.

The regulation reservoir 313 is preferably provided with means 313a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 26 and 27a-c. The block diagram shown in FIG. 26 comprises with a first closed system controlling a second closed system. The first system comprises a regulation reservoir 313 and a servo reservoir 350. The servo reservoir 350 mechanically controls a larger adjustable reservoir 352 via a mechanical interconnection 354. An implanted apparatus 10 having an expandable/contactable cavity is in turn controlled by the larger adjustable reservoir 352 by supply of hydraulic fluid from the larger adjustable reservoir 352 in fluid connection with the apparatus 10.

Figure 27:
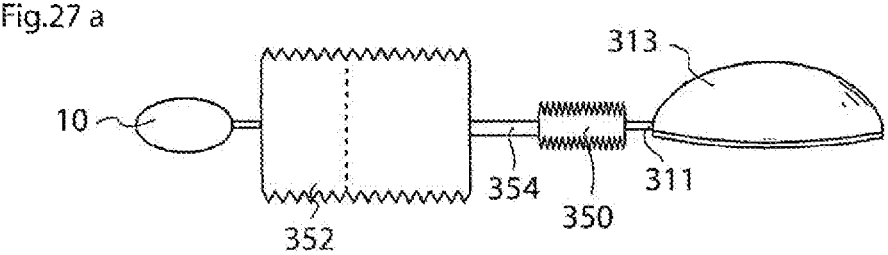
Figure 27:
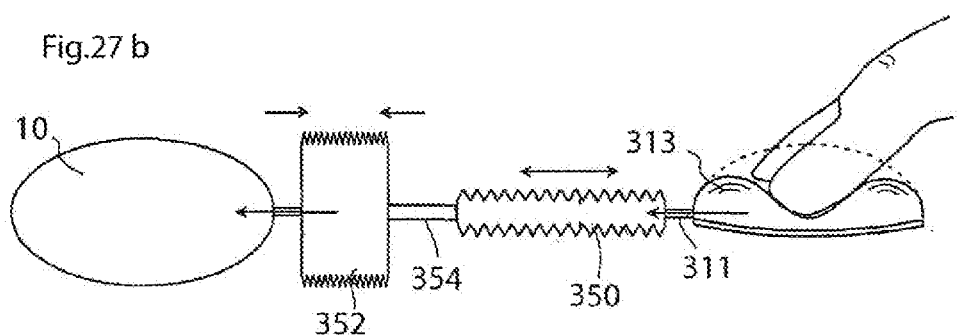
Figure 27:
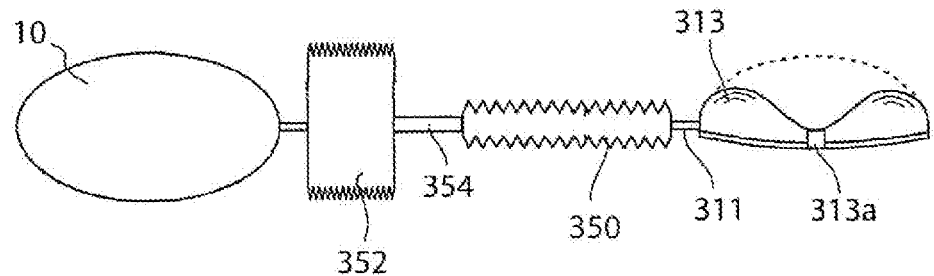

An example of this embodiment will now be described with reference to FIG. 27a-c. Like in the previous embodiment, the regulation reservoir is placed subcutaneous under the patient's skin and is operated by pushing the outer surface thereof by means of a finger. The regulation reservoir 313 is in fluid connection with a bellow shaped servo reservoir 350 by means of a conduit 311. In the first closed system 313, 311, 350 shown in FIG. 27a, the servo reservoir 350 contains a minimum of fluid and most fluid is found in the regulation reservoir 313.

The servo reservoir 350 is mechanically connected to a larger adjustable reservoir 352, in this example also having a bellow shape but with a larger diameter than the servo reservoir 350. The larger adjustable reservoir 352 is in fluid connection with the apparatus 10. This means that when a user pushes the regulation reservoir 313, thereby displacing fluid from the regulation reservoir 313 to the servo reservoir 350, the expansion of the servo reservoir 350 will displace a larger volume of fluid from the larger adjustable reservoir 352 to the apparatus 10. In other words, in this reversed servo, a small volume in the regulation reservoir is compressed with a higher force and this creates a movement of a larger total area with less force per area unit.

Like in the previous embodiment described above with reference to FIGS. 25a-c, the regulation reservoir 313 is preferably provided with means 313a (FIG. 27c) for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Other features and uses of the invention and their associated advantages will be evident to a person skilled in the art upon reading the description.

It is to be understood that this invention is not limited to the particular embodiments shown here. The scope of the present invention is limited only by the appended claims and equivalents thereof.

The invention claimed is:

1. An apparatus for implantation in a sexually responsive tissue of a vulva of a patient, the apparatus comprising at least one expandable prosthesis configured to temporarily achieve enlarged status of a female erectile tissue and a stimulation device for creating vibrations placed inside said expandable prosthesis, wherein the said expandable prosthesis defines an enclosed volume, the stimulation device being provided within said enclosed volume.

2. The apparatus according to claim 1, wherein the expandable prosthesis is adapted to be expanded by hydraulic fluid.

3. The apparatus according to claim 1, wherein the stimulation device comprises an eccentric mechanism causing movement of the hydraulic fluid.

4. The apparatus according to claim 1, further comprising at least one reservoir in fluid connection with the expandable prosthesis.

5. The apparatus according to claim 1, further comprising at least one switch implantable in the patient.

6. The apparatus according to claim 1, further comprising a wireless remote control.

7. The apparatus according to claim 1, further comprising an implantable hydraulic reservoir, hydraulically connected to the apparatus, and adapted to be regulated by manually pressing the hydraulic reservoir.

8. The apparatus according to claim 1, wherein the apparatus is adapted to be energized non-invasively by at least one of; an implanted internal energy source, and non-invasively and wirelessly by an energy transmission device from outside the patient's body sending wireless energy to an internal energy receiver.

9. The apparatus according to claim 1, comprising a sensor and/or a measuring device sensing or measuring at least one physical parameter of the patient.

10. The apparatus according to claim 1, comprising a sensor and/or a measuring device sensing or measuring at least one functional parameter related to the apparatus.

11. The apparatus according to claim 1, further comprising an implantable internal control unit and a feedback device for sending feedback information from inside the patient's body to the outside of the patient's body.

12. The apparatus according to claim 1, where the stimulating device is adapted to create hydraulic movement with an amplitude from 0.01 to 30 mm.

13. The apparatus according to claim 1, further comprising a control device for manually controlling the at least one stimulating device from outside the patient's body.

14. The apparatus according to claim 1, further comprising a control device for controlling the intensity of the stimulation device.

15. The apparatus according to claim 1, comprising a control device for independently controlling amplitude and frequency of the movement.

16. The apparatus according to claim 1, wherein the stimulation device comprises an eccentric mechanism.

17. The apparatus according to claim 1, wherein the stimulation device comprises an electromagnetic mechanism.

* * * * *